United States Patent [19]
Hanson

[11] Patent Number: 5,184,954
[45] Date of Patent: Feb. 9, 1993

[54] ELASTOMERIC ORTHODONTIC TRACTION RIBBON SPRINGS

[75] Inventor: G. Herbert Hanson, Hamilton, Canada

[73] Assignee: Hamilton Ortho Inc., Hamilton, Canada

[21] Appl. No.: 795,139

[22] Filed: Nov. 20, 1991

Related U.S. Application Data

[63] Continuation-in-part of Ser. No. 661,969, Feb. 28, 1991, abandoned.

[51] Int. Cl.⁵ .............................................. A61C 3/00
[52] U.S. Cl. .................................... 433/18; 433/11
[58] Field of Search ................ 433/18, 21, 22, 23, 433/11, 15, 8, 141, 3

[56] References Cited

U.S. PATENT DOCUMENTS

| | | | |
|---|---|---|---|
| 3,803,715 | 4/1974 | Wallshein | 433/18 |
| 3,896,549 | 7/1975 | Wallshein | 433/18 |
| 3,903,601 | 9/1975 | Anderson | 433/18 |
| 3,961,421 | 6/1976 | Wallshein | 433/18 |
| 3,987,547 | 10/1976 | Moss | 433/18 |
| 4,054,997 | 10/1977 | Wallshein | 433/11 |
| 4,416,627 | 11/1983 | Beazley | 433/18 |
| 4,614,497 | 9/1986 | Wallshein | 433/8 |
| 5,005,730 | 4/1991 | Pickrell, Jr. | 221/71 |

*Primary Examiner*—Gene Mancene
*Assistant Examiner*—Cindy A. Cherichetti
*Attorney, Agent, or Firm*—Rogers & Scott

[57] ABSTRACT

An elastomeric traction ribbon spring for use in orthodontic procedures consists of a thin and narrow ribbon of substantially constant thickness and width along the length of its operative portion, which is provided with a centrally disposed row of relatively small relatively closely spaced holes extending through its thickness dimension. The tension applied between two anchor points is adjusted by choice of the holes engaged at these points. A specific example is 0.9 mm (0.035in) wide and 0.3 mm (0.012in) thick with holes of 0.2 mm (0.008in) diameter spaced 0.58 mm (0.023in) apart center to center. Each hole may have at the underface a funnel-shaped recess that facilitates mounting of the ribbon on its anchor point; a method of forming such holes is provided using an apertured die and a concentric pointed punch. The spring may be supplied in a long length from which the required amount is cut. Alternately they may be in separate lengths each with a finger-gripping part at one end; the distal end may be provided with a larger hole to facilitate attachment to the distal anchor point, while the mesial end may have a hole for temporary attachment of a tension meter. A particularly suitable anchor is a post with an enlarged head, the ribbon being forced over the head, which may be ball- or mushroom-shaped. A tool with a cup-shaped head is provided to facilitate forcing the ribbon over the enlarged head when it is inaccessible by hand.

26 Claims, 4 Drawing Sheets

ELASTOMERIC ORTHODONTIC TRACTION RIBBON SPRINGS

This application is a continuation-in-part of my prior application Ser. No. 07/661,969, filed 28th Feb. 1991, now abandoned.

FIELD OF THE INVENTION

This invention provides new elastomeric traction ribbon springs for use in orthodontic procedures, new combinations of such ribbon springs with orthodontic appliances, new methods of making such ribbon springs, and new tools for use with such ribbon springs.

REVIEW OF THE PRIOR ART

Elastomeric traction loop elastics are now widely used in orthodontic procedures since they are relatively simple and inexpensive to use and to replace if they become ineffective or broken, and can readily by made in a wide variety of lengths and thicknesses to give a correspondingly wide choice of traction forces. One form taken by such elastics is a large single loop which is stretched between two anchor points provided by hooks on two spaced orthondontic appliances mounted on respective teeth, for example two brackets or a bracket and a buccal tube. Such elastics are used intermaxillarly between the upper and lower jaws, or intramaxillarly between two anchor points both on the upper jaw, or intramandiblarly between two anchor points both on the lower jaw. The elastics are somewhat unhygenic in that they create numerous traps for food and plaque to accumulate and, since they are usually made of latex, they tend to deteriorate relatively quickly in the hostile chemical environment of the mouth.

A recently-developed form of elastomeric traction device consists of a chain of small circular loops, each immediately adjacent pair of the loops being joined together either edge to edge along a common chord or by a connecting portion of smaller width; in both cases the connection is thus of smaller width than the loops in order to provide the necessary tension/elongation characteristic. Each loop is sufficiently large to engage around a bracket body as the respective anchor point, or around a pair of tie wings on a bracket body, the traction force being adjusted by choice of the number of unengaged loops between the two anchor points. In one such chain the loops are of about 2.85 mm (0.112 in) diameter with apertures of 1.27 mm (0.050 in) diameter. The common chordal junctions between them are about 1.40 mm (0.055 in) wide, while the chain is of uniform thickness and 0.48 mm (0.019 in) thick. In a chain in which the loops are spaced apart they are of about the same dimensions, while the connections between them are about 1.27 mm (0.050 in) wide and about 1 mm (0.04 in) long. These chains are not only used as tension springs, but are also used stretched over the tie wings of conventional winged brackets so as to retain the tie wire in the bracket slots. Owing to their configuration and the size and spacing of the loops it is often found that it is not possible to arrange for them to provide any traction, except at extraction sites or where the teeth are large. It is also somewhat difficult to regulate the traction force between adjacent teeth, again because of their configuration, but they are proving to be quite satisfactory for their specific intended purposes and are widely used.

DEFINITION OF THE INVENTION

It is the principal object of the present invention to provide a new form of elastomeric traction ribbon spring having wide application in orthodontic procedures.

It is another object to provide such a ribbon spring that is particularly effective in cooperation with specifically adapted anchor means provided on the orthodontic devices with which they are to be used.

It is a further object to provide a method of manufacture of the new elastomeric traction ribbon springs.

It is a further object to provide a new tool that facilitates the application of the new elastomeric traction ribbon springs to anchor means with which they are employed.

In accordance with the invention there is provided an elastomeric traction ribbon spring comprising:

a ribbon of elastomeric material of substantially uniform width and thickness along the length of its spring operative portion, the ribbon having along the length of the operative portion a single row of longitudinally spaced holes, the holes being of diameter in the range from 0.13 mm (0.005 in) to 0.5 mm (0.020 in), and being spaced longitudinally centre to centre from 0.4 mm (0.016 in) to 1.5 mm (0.060 in) with a minimum edge to edge hole spacing of 0.2 mm (0.008 in).

Preferably the spring has a maximum width of about 1.6 mm (0.060 in) and has a maximum thickness of about 0.63 mm (0.025 in).

Preferably each hole is provided at the underside face with a respective funnel-like recess leading from the underside or occlusal face of the ribbon to the remainder of the hole.

Preferably the holes are of diameter 0.2 mm (0.008 in), and preferably they are spaced longitudinally centre to centre from 0.5 mm (0.020 in) to 1.00 mm (0.040 in); more specifically preferably they are spaced longitudinally centre to centre 0.58 mm (0.023 in).

The traction ribbon spring preferably is used in combination with an orthodontic device having as attachment means for the spring a post protruding from a surface thereof with an enlarged head of greater diameter than the post, the post protruding from the device. The ribbon spring is forced over the enlarged head post against its resilience until it embraces the smaller diameter post and is retained by the head against removal from the post.

Also in accordance with the invention there is provided an orthodontic tool for use in attachment of a traction spring comprising a ribbon of resilient material with a row of longitudinally spaced holes therein to attachment means of an orthodontic device, the attachment means comprising a post having an enlarged head, the tool comprising a handle portion and a cup-shaped portion having therein a recess of diameter to pass over the enlarged head, the recess being of depth to receive the enlarged head, whereby a portion of a ribbon having a hole engaged with the enlarged head and engaged by the cup-shaped portion can be forced by the tool over the enlarged head until the ribbon embraces the smaller-diameter post.

Further in accordance with the invention there is provided a method of making an elastomeric traction ribbon spring comprising a continuous ribbon of elastomeric material of substantially continuous width and thickness along its length, the ribbon having along its length a single row of longitudinally spaced holes, the holes each having its underside face a respective funnel-like recess leading from the underside face of the ribbon to the remainder of the hole, the method including the steps of:

disposing the ribbon on an apertured die member having therein a sharp-edged aperture;

forcing into the ribbon and into the aperture concentrically therewith a conically tipped pointed punch of triangular transverse cross-section to force the resilient material of the ribbon into the aperture and thereafter to sever a piece of the ribbon thus forced into the aperture by engagement between the punch conical tip and the edge of the aperture to form such a hole with a funnel-like recess at the ribbon underside face.

DESCRIPTION OF THE DRAWINGS

Particular preferred embodiments of the invention will now be described, by way of example, with reference to the accompanying diagrammatic drawings wherein.

DESCRIPTION OF THE PREFERRED EMBODIMENTS

Figure 1:
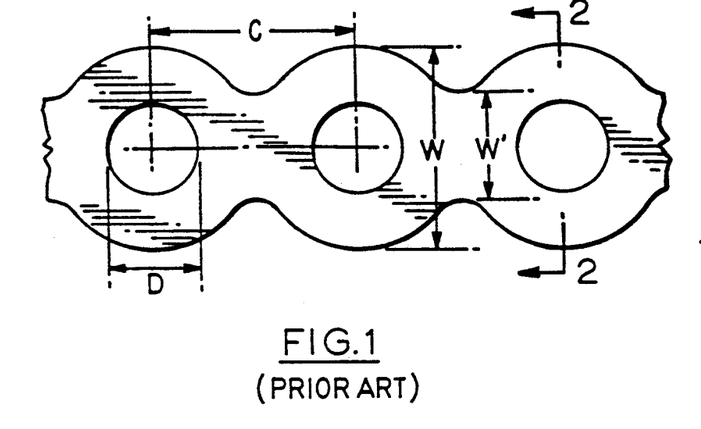
FIG. 1 is an elevation in plan of part of a prior art traction spring chain consisting of edge-to-edge joined loops, the spring being shown in relaxed unextended state.
Figure 2:
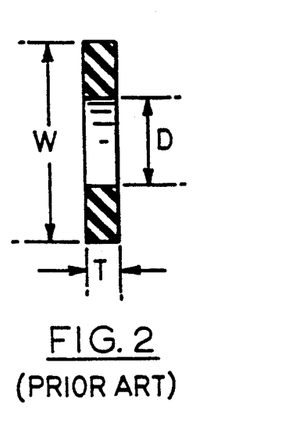
FIG. 2 is a cross-section through the prior art chain of FIG. 1 taken on the line 2—2 of FIG. 1.
Figure 3:
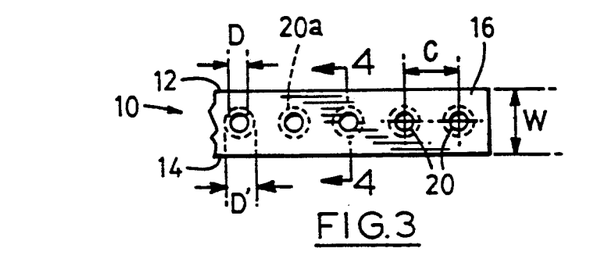
FIG. 3 is an elevation in plan similar to FIG. 1 of a first embodiment of a traction ribbon spring of the invention, the spring also being shown in relaxed unextended state, and the Figure being drawn to the same scale as FIG. 1 in order to illustrate the relative sizes of the two devices.
Figure 4:
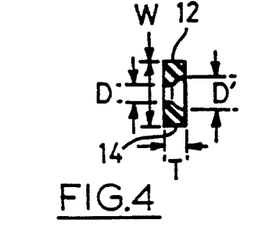
FIG. 4 is a cross-section through the ribbon spring of FIG. 3 taken on the line 4—4 of FIG. 3.
Figure 5:
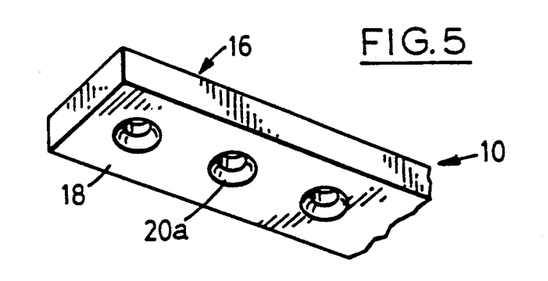
FIG. 5 is a perspective view of the underside of the ribbon spring of FIGS. 3 and 4.

A typical prior art traction spring chain is illustrated by FIGS. 1 and 2 and consists of a series of circular loops connected edge-to-edge. As described above in the review of the prior art, such a chain typically is of material of uniform thickness T of about 0.48 mm (0.019 in). The maximum width W of the chain is determined by the diameter of the individual loops which in this embodiment is 2.85 mm (0.112 in). The apertures are of 1.27 mm (0.050 in) diameter D and are spaced centre-to-centre C by 2.92 mm (0.115 in). If the side edges of the loops were projected to be complete circles the adjacent circles would just touch edge-to-edge, but the connecting portion is widened to provide the required tension/extension spring characteristic, and in this embodiment the common chordal junction or "neck" between adjacent loops has a width W of 1.40 mm (0.055 in). Typically when fully extended the thickness T has reduced to 0.38 mm (0.015 in), width W has reduced to 1.54 mm (0.060 in), while neck width W has reduced to 1.14 mm (0.045 in). The circular apertures are now elongated ellipses of major chord length 3.9 mm (0.155 in), minor chord length 0.48 mm (0.019 in) and centre-to-centre spacing C of 5.58 mm (0.220 in). These parameters W, T, D and C are also used below in describing the embodiments of the invention.

Figure 6:
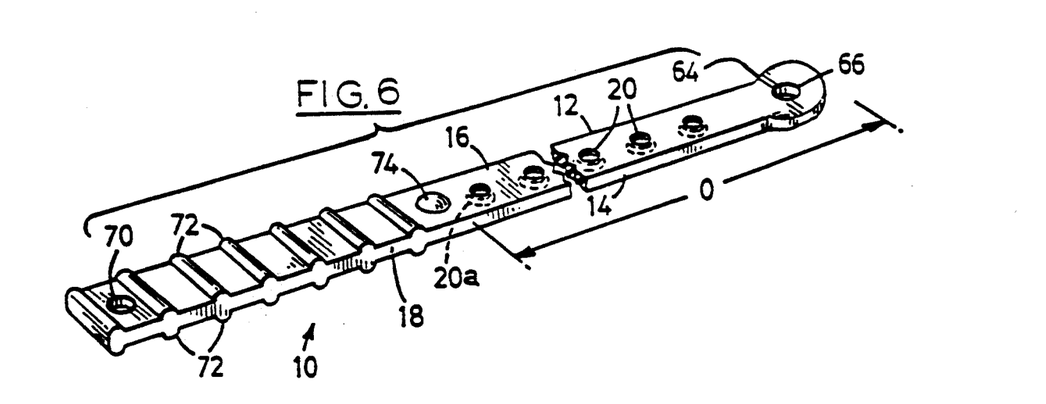
FIG. 6 is a perspective view of a ribbon spring of the invention, also shown in relaxed unextended state, and illustrating one specific form of the device as supplied to orthodontists.
Figure 7:
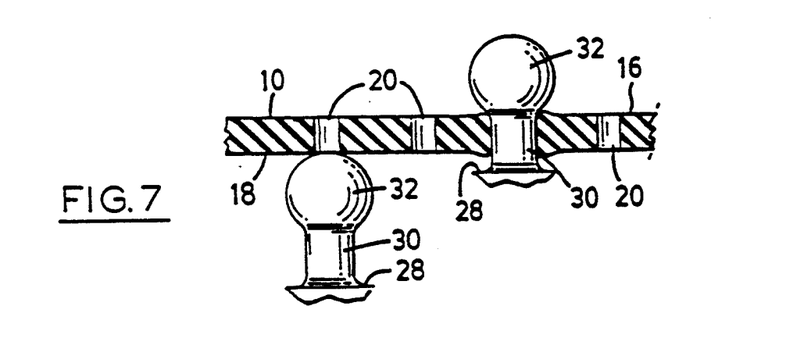
FIG. 7 is a longitudinal cross-section through part of a ribbon spring which is another embodiment of the invention, the Figure illustrating the manner of mounting the spring on a spherical ball-ended post.

The elastomeric traction ribbon springs of the invention can be supplied to the orthodontist in a number of different forms, depending on the preference of the individual practitioner. For example, it can be provided in the form of a spool thereof of a length of about 15 meters (50 feet), from which the orthodontist cuts the amount required for the intended procedure; if too long the piece can be cut to the final required length once installed in the patient's mouth using a sharp ligature cutter. Alternatively, as illustrated by FIG. 6, it can be supplied as preformed lengths which will be described in more detail below. In relaxed unextended state the traction spring consists of a continuous ribbon 10, preferably of rectangular cross-section, the operative spring portion of which is of substantially uniform width W between parallel side faces 12 and 14 and substantially uniform thickness T between parallel top and bottom faces 16 and 18, the ranges of values of which will be reviewed below. The longitudinal edges between these faces may be slightly rounded without substantial change in the tension/extension characteristic of the spring material. The ribbon is provided along its length with a single central row of longitudinally spaced holes 20 formed in the ribbon width dimension W and thus extending between the top and bottom faces, the longitudinal axes of the holes being spaced equidistantly from the side faces 12 and 14. In the embodiment of FIGS. 3-6 the portion of each hole 20 extending from the top of the gingival face 16 is of diameter D, while each hole is provided extending from the underside or occlusal surface 18 with a counter-recess 20a of diameter D' at the occlusal face. In the embodiment of FIG. 7 these holes are cylindrical along their full length and of diameter D. In both embodiments the holes are spaced longitudinally from one another centre to centre a distance C. The ranges of values of these parameters W, T, D, D' and C will be reviewed below. For convenience in manufacture and operation the longitudinal spacing of the holes will usually be uniform, but this need not be the case, and in some embodiments the spacing may vary between successive holes, and such variation may itself be in some regular pattern.

FIG. 6 illustrates a specific form of the devices of the invention in which they may be delivered to the orthodontist in place of the coil described above. Each separate device consists of a spring operative portion 0 which is the portion that is provided with the row of apertures 20. The distal end 64 is widened somewhat and is provided with a slightly larger diameter hole 66, which is therefore easier to engage with an attachment device located deep within the patient's mouth. The part of the operative portion O immediately adjacent to this hole 66 need not be perforated, since there will always be a minimum length required in extending between the distal anchor found on one tooth and the corresponding mesial anchor found on another tooth. The mesial end 68 is unperforated except for a larger hole 70 at its extreme end which permits attachment to the device of a tensionmeter (not illustrated) that the orthodontist can use to measure the tension in the spring as the selected hole 20 is engaged with the mesially-disposed attachment point. The unperforated mesial portion is provided with a plurality of longitudinally-spaced transverse ribs 72 which facilitate the gripping of the spring by the orthodontist's fingers or by a gripping tool such as a pair of pliers; this portion is of course severed as described above for the continuous version once the spring is in place. The versions of the device in which the holes 20 are provided with counter-recesses 20a can also be provided at the gingival face 16 with a gingival protrusion or bump 74 that enables the orthodontist to identify that face by feel alone.

FIGS. 7 to 11 and 15 illustrate a preferred form of attachment means for orthodontic devices to facilitate use of these traction ribbon springs with such devices. The device may for example be a buccal tube, or an orthodontic bracket of the type disclosed and claimed in my prior U.S. Pat. No. 4,492,573, the disclosure of which is incorporated herein by this reference. The bracket body 28 has rigidly attached to its gingival surface a gingivally-lingually protruding post 30 that, in the embodiment of FIG. 7, terminates in a spherical ball 32, the post and ball being smooth and polished to a mirror finish. As is shown in FIG. 7, a traction ribbon spring of the invention is attached to the post simply by forcing the ball 32 through the chosen hole 20 until the spring embraces the post, as shown to the right of the Figure, when it is held securely, the post-mounted ball thus performing the same function on the bracket as the hooks used hitherto with known springs and attachment devices.

FIGS. 8–11 illustrate another shape for the enlarged post end 36, referred to for convenience in terminology as a mushroom-shaped end. As will be seen from the Figures the post end 36 has the top surface 36a, which is the surface that first engages the spring counter-recess 20a, of relatively small radius r (FIG. 10), while the under surface 30b between the top surface and the post has a relatively large radius R, or the equivalent to such a radius, so that the surface 36b forms a shoulder or overhang that establishes the mushroom shape. The small radius top surface 36a thus continues to facilitate the passage of the post through the spring 10, while the large radius overhang surface 30b positively inhibits its removal. In the extreme case the surface 30b would be flat (i.e. R is infinite) but in practice, especially in the small sizes employed in orthodontics, there will be a somewhat rounded junction between the surfaces 36a and 36b, and also between the surface 36b and the cylindrical post surface, to give the effect of a surface of relatively large radius. With this mushroom shaped head the ribbon spring is somewhat more securely attached to the post, and this may be preferable when the tension required for the procedure is very low, and/or there is strong tendency for the ribbon spring to be pulled off the attachment means (i.e. when sticky foods are eaten).

The traction ribbon springs of the invention are, as illustrated, much smaller in transverse dimensions than the above-described prior art loop chain springs, and are therefore less conspicuous in the patient's mouth and more cosmetically attractive. When used with my brackets referred to above they can be kept out of contact with the arch wire and therefore do not introduce undesired and unpredictable friction which can impede the progress of the procedure. Because of their uniform rectangular, external shape they have less possibility of collecting food particles and plaque and are therefore more hygenic. Because of their highly uniform cross-section along their length they are of more uniform stress/elongation characteristic than the prior art chains, and it is therefore easier for the orthodontist to estimate the length of chain that is required. With suitable choice of materials they can be elongated until they are stretched very thin, until they are near to the elastic limit, without generating excessive force. Because of the large number of holes in even a short length of the material there is a wide range of choice of extension and therefore the traction force, and this can easily be rapidly adjusted by moving the point of attachment from hole to hole. For example, the average spacing bracket to bracket in the human mouth varies between 2 mm (very small teeth) and 7 mm, and an embodiment of 0.2 mm hole diameter at 0.58 mm spacing will be able to apply traction even across the smaller dimension, while it will have 10 holes between any two usual attachment points for the larger dimension when relaxed. The number of holes is of course vastly increased when the spring spans an extraction opening (as many as 20) and/or a number of teeth. It is found in orthodontic practice that because of their small cross-section it is easier with these new springs to avoid contact with the arch wire, so that there is less possibility of friction that would impede the procedure and wear the elastomer.

Figure 8:
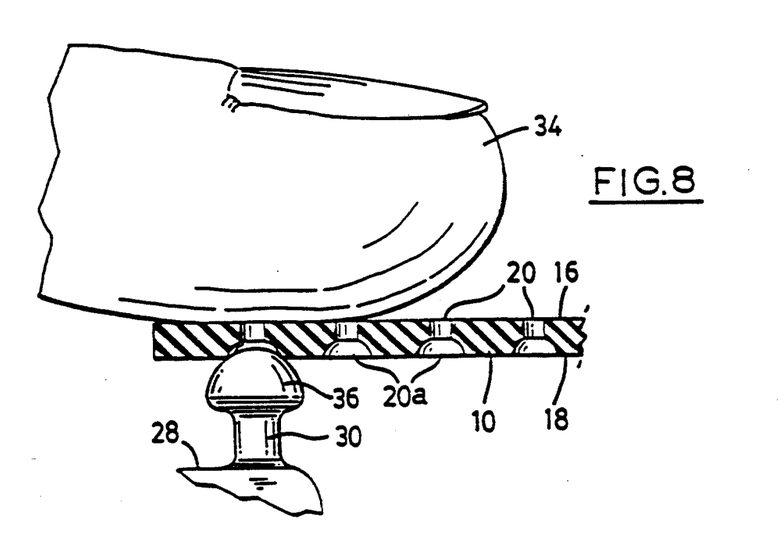
FIGS. 8, 9 and 10 are part elevation, part longitudinal cross-section progressive views illustrating the mounting of the ribbon springs of FIGS. 3-6 on a mushroom-ended post.
Figure 9:
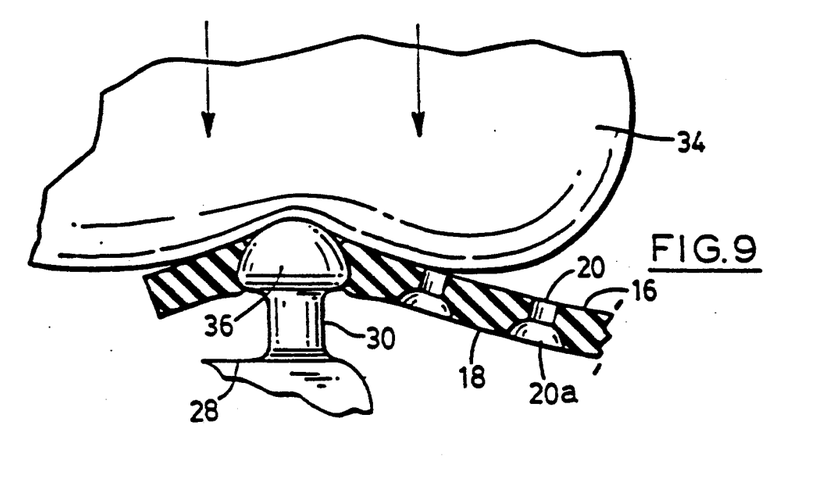
Figures 10, 11:
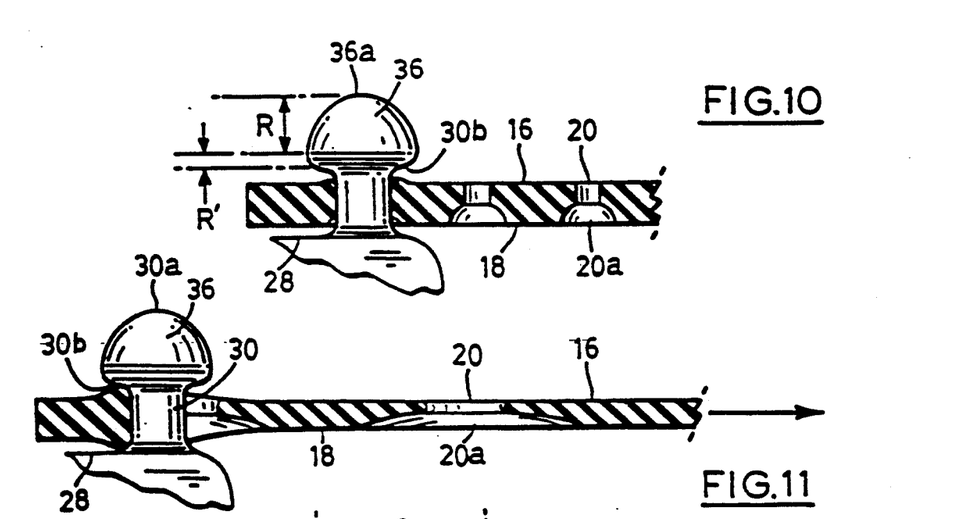
FIG. 11 shows the effect of elongation on the ribbon spring of FIGS. 3-6.

In the embodiments in which the holes 20 are provided with funnel-like counter-recesses 20a each counter-recess preferably is of smoothly rounded progressively inwardly tapering shape, more specifically preferably of part spherical shape, as illustrated by the Figures. These funnel counter-recesses facilitate the engagement of the selected hole with the enlarged post end, as illustrated by FIG. 8, and also facilitate the pressing of the spring 10, as by the orthodontist's finger 34, downwards over the enlarged post end, as illustrated by FIG. 9, until it is embracing the post 30, as illustrated by FIGS. 10 and 11, the latter figure illustrating the shape taken by the ribbon spring and the holes when under tension. The ratio of the value of the axial dimension E (FIG. 12) of each counter-recess to the thickness T of the ribbons is not critical and the minimum value will be about 0.2 in order to provide a sufficiently large funnel recess for ready engagement with the post end; the usual range of values is about 0.4 to 0.6 and the preferred value is about 0.5. It is not necessary for the funnel recesses to be rounded in cross-section and progressively tapering triangular cross-section recesses would also be satisfactory. The exit diameter D' of the funnel mouth at the lower spring face 18 will usually be of the order of 1.5–3 times the value of D and preferably is about 2 times that value.

The preferred range of the hole diameters (or minimum transverse dimension which will be the equivalent to diameter for holes that are not completely cylindrical) and of the longitudinal spacings of the holes are discussed below. The tension/extension characteristics of the individual springs depend mainly on the transverse cross-section areas of the ribbon in the planes where the distances between the side walls 12 and 14 and the hole side walls are at their respective minimums. It is desired to keep the width and thickness dimensions W and T as small as possible and the values that are selected will also depend to a considerable extent on the physical properties of the elastomeric material used. The wide adoption of elastomeric springs has been accompanied by considerable effort to develope materials that are suitable for use in the demanding and hostile conditions encountered in orthodontic procedures. Preferably the materials are as transparent as possible to improve the cosmetic appearance. A suitable transparent material is, for example, that sold by Toyo Miura K.K. under the trademark "F.M. SUPERTHREAD". Elastomeric ribbons of different cross-section areas will be used dependent upon the amounts of elongation and traction that are required, and the following table gives a suitable estimated range of sizes using the material specified. The dimensions are given in millimeters with the equivalent inch values in parentheses.

TABLE

| | Wmm | Tmm | Dmm | Cmm | Fmm | E % |
|---|---|---|---|---|---|---|
| A | 1.50 (0.060) | 0.50 (0.020) | 0.50 (0.020) | 0.84 (0.033) | 1.00 (0.040) | 0.5 |
| B | 1.25 (0.050) | 0.50 (0.020) | 0.38 (0.015) | 0.84 (0.033) | 0.76 (0.030) | 0.5 |
| C | 1.00 (0.040) | 0.38 (0.015) | 0.25 (0.010) | 0.84 (0.033) | 0.50 (0.020) | 0.5 |
| D | 0.90 (0.035) | 0.30 (0.012) | 0.20 (0.008) | 0.58 (0.023) | 0.40 (0.016) | 0.5 |
| E | 0.90 (0.035) | 0.30 (0.012) | 0.13 (0.005) | 0.58 (0.023) | 0.26 (0.010) | 0.5 |

Figure 12:
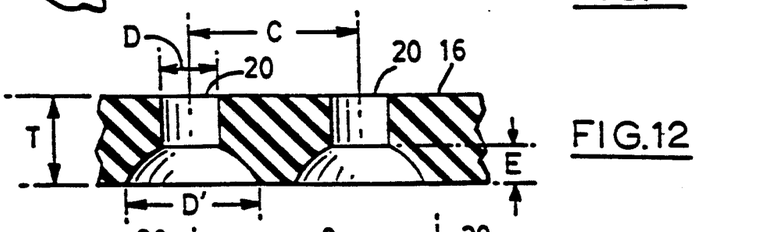
FIGS. 12 and 13 are longitudinal cross-sections through two different variations of the embodiment of FIGS. 3-6, showing different possible hole sizes and spacings.
Figure 13:
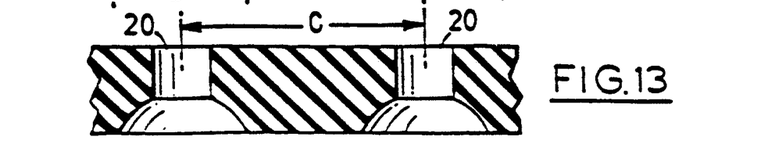

The maximum value of W that is contemplated for the ribbon is about 1.5 mm (0.060 in), while the maximum value of T is about 0.63 mm (0.025 in). The preferred range of sizes of the holes 20 is relatively limited and is between 0.13 mm (0.005 in) and 0.5 mm (0.020 in), with the preferred value being 0.20 mm (0.008 in). As described above, it will be understood that the holes need not be truly circular in cross-section in planes parallel to the faces 16 and 18, although this is preferred, and it is convenient to express their transverse cross-section size by reference to their diameter, or to their equivalent diameter if not circular. The longitudinal spacing of the holes can vary much more widely, but with the practical limitation that they should not usually be spaced closer to one another edge-to-edge than about 0.2 mm (0.008 in) so as to provide sufficient elastic material between them; with purely cylindrical holes of minimum diameter 0.2 mm this imposes a minimum centre to centre spacing of 0.4 mm (0.016 in). The preferred upper limit for longitudinal spacing is 1.5 mm (0.06 in), a preferred range is from 0.5 mm (0.020 in) to 1.00 mm (0.040 in); a more preferred range is from 0.38 mm (0.015 in) to 0.63 mm (0.025 in); a particularly preferred value is 0.58 mm (0.023 in). With closely spaced holes 20 as illustrated by FIG. 12 the minimum spacing between the funnel recesses 20a will be 0.13 mm (0.005 in), while with the widely spaced holes of FIG. 13 the spacing between the funnel recesses can be 0.38 mm (0.015 ins).

The post 26 preferably has a shaft diameter in the range of about 0.3 mm to about 0.75 mm (0.012 in to 0.03 in), and preferably is about 0.5 mm (0.02 in) diameter, while the enlarged end 32 or 36 has a diameter (for surface 36a of end 36) in the range of about 0.60 mm to about 1.2 mm (0.024 in to 0.048 in), the diameter of the end usually increasing corresponding to an increase in diameter of the shaft, with the mushroom-shaped end 36 usually having the surface 36a of larger diameter than the corresponding end surface of the ball-shaped end 32. The overall length of the shaft-mounted enlarged end will be from about 0.075 mm to about 0.150 mm (0.030 in to 0.060 in) and its palatol inclination lingually to the gingival/occlusal axis will range from about +10° to about −20°, depending upon the tooth to which it is to be attached. Such enlarged-end shaft attachments can be made smaller and are more attractive cosmetically than the usual attachment hooks; in addition they completely avoid any sharp edges that are encountered with conventional hooks. They also permit the springs to be applied vertically intermaxillarly between two devices on different sets of teeth.

Figure 14:
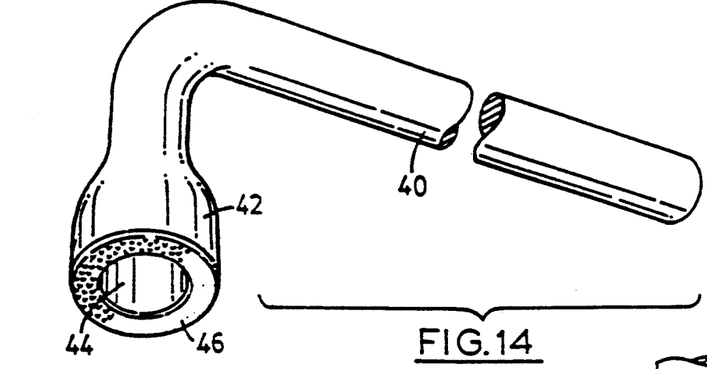
FIG. 14 is a perspective view from below of the operative end of a tool facilitating the mounting of a ribbon spring of the invention on a headed post.
Figures 15, 16:
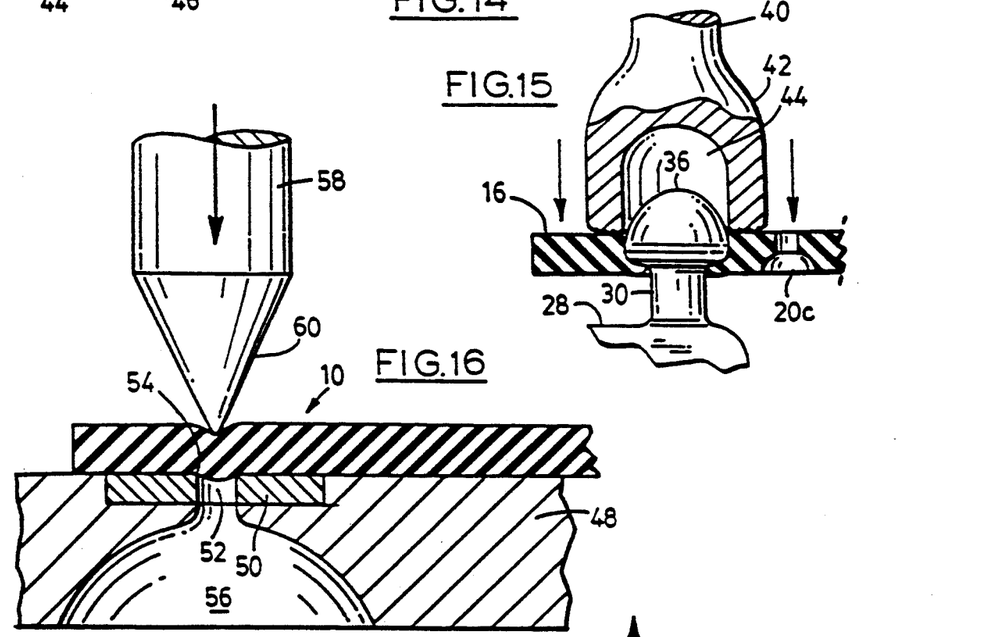
FIG. 15 is a part elevation, part cross-section, illustrating the mode of operation of the tool of FIG. 14.
FIGS. 16, 17 and 18 are progressive views showing one method of producing the traction ribbon springs of FIGS. 3-6.

FIGS. 14 and 15 illustrate a tool that can be used by the orthodontist for the ready installation of the ribbon springs of the invention when the location is difficult of access by the finger when attempting to use the installation procedure illustrated by FIGS. 8 and 9. The tool has a handle 40 and a cup-shaped end portion 42 with an open-ended recess 44, the cup fitting over the enlarged post end 32 or 36 and being deep enough to receive the post into its interior. The annular face 46 of the portion 42 that engages the ribbon surface 16 has the semi-annulus further from the handle 40 serrated or otherwise roughened, while the semi-annulus adjacent the handle is smooth. As illustrated by FIG. 14, as the cup-shaped portion forces the spring over the post end 36 the roughened portion of the face 46 holds the spring, while the smooth portion allows the spring to stretch and slide beneath it as the spring is installed.

Figure 17:
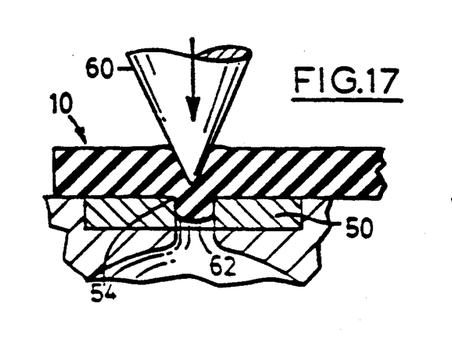
Figure 18:
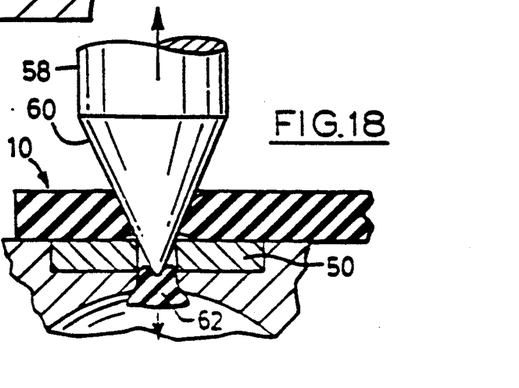

FIGS. 16 to 18 illustrate a method of making the funnelled openings 20 and 20a by a single punching operation. The ribbon 10 is laid on a support 48 with the ribbon occulsal surface in contact with an anvil portion 50 of hard material, such as tungsten carbide, provided with a central hole 52 having an edge 54 that is as sharp as possible, the hole 52 opening into a relatively large counter-recess 56. A cylindrical punch 58 having a conical tip 60 of transverse triangular cross-section is centred as accurately as possible over the hole 52 and is then forced into the strip 10 and into the hole until the conical face of the tip engages the edge 54. The initial movement of the punch tip into the ribbon forces elastomeric material into the hole from the occlusal side of the ribbon and, when a block 62 of material eventually is severed from the ribbon as the punch tip engages sharp edge 54, this block is found to have the shape that upon separation will leave behind the desired funnelled aperture 20 and 20a.

I claim:

1. An elastomeric traction ribbon spring for connection between two spaced orthodontic devices attached to respective teeth in a patient's mouth and resultant application of tension between the two devices, the spring comprising:

a ribbon of elastomeric material of substantially uniform width and thickness along the length of its spring operative portion, the maximum width of the spring operative portion being 1.5 mm and the maximum thickness of the spring operative portion being 0.6 mm, the ribbon having along the length of the spring operative portion a single row of longitudinally spaced holes, the holes being of diameter in the range from 0.13 mm to 0.5 mm, and being spaced longitudinally centre to centre from 0.4 mm to 1.5 mm with a minimum edge to edge hole spacing of 0.2 mm.

2. A traction ribbon spring as claimed in claim 1, wherein each hole is provided at the occlusal underside face of the ribbon with a respective funnel-like recess leading from the occlusal underside face to the remainder of the hole.

3. A traction ribbon spring as claimed in claim 2, wherein the diameter of the funnel recess mouth at the occlusal underside face is from 1.5 to 3 times the diameter of the hole.

4. A traction ribbon spring as claimed in claim 2, wherein the mesial end of the operative portion is provided on its gingival face with a gingival protrusion to facilitate identification of that face.

5. A traction ribbon spring as claimed in claim 1, wherein the holes are of diameter 0.2 mm.

6. A traction ribbon spring as claimed in claim 5, wherein the holes are spaced longitudinally centre to centre 0.58 mm.

7. A traction ribbon spring as claimed in claim 1, wherein the holes are spaced longitudinally centre to centre from 0.5 mm to 1.00 mm.

8. A traction ribbon spring as claimed in claim 1, and comprising at the mesial end of the operative portion an unperforated gripping portion to facilitate handling of the spring.

9. A traction ribbon spring as claimed in claim 1, wherein the mesial end of the spring is provided with a hole that is larger in diameter than the holes of the operative portion for attachment of a tension meter thereto.

10. A traction ribbon spring as claimed in claim 1, in combination with an orthodontic device having as attachment means for the spring a post protruding from a surface thereof with an enlarged head of greater diameter than the post, over which enlarged head the spring is forced against its resilience until it embraces the smaller diameter post and is retained by the head against removal from the post.

11. A traction ribbon spring as claimed in claim 10, wherein the enlarged head is of ball shape.

12. A traction ribbon spring as claimed in claim 10, wherein the enlarged head is of mushroom shape with a radially extending shoulder between the post and the remainder of the head.

13. A traction ribbon spring as claimed in claim 10, wherein the orthodontic device is an orthodontic bracket.

14. A traction ribbon spring as claimed in claim 1, in combination with an orthodontic tool for use in attachment of the spring to orthodontic device attachment means comprising a post with an enlarged head, the tool comprising a handle portion and a cup-shaped portion, the cup-shaped portion having therein a recess of diameter to pass over the enlarged head, the recess being of depth to receive the enlarged head, whereby a portion of the ribbon having a hole engaged with the enlarged head and engaged by the cup-shaped portion can be forced by the tool over the enlarged head.

15. A traction ribbon spring as claimed in claim 14, wherein the cup-shaped member has an annular surface surrounding the recess with a semi-annular portion thereof roughened for non-slip engagement with the material of the ribbon.

16. An elastomeric traction ribbon spring for connection between two spaced orthodontic devices attached to respective teeth in a patient's mouth and resultant application of tension between the two devices, the spring comprising:

a ribbon of elastomeric material of substantially uniform width and thickness along the length of its spring operative portion, the ribbon having along the length of the spring operative portion a single row of longitudinally spaced holes, the holes being of diameter in the range from 0.13 mm to 0.5 mm, and being spaced longitudinally centre to centre from 0.4 mm to 1.5 mm with a minimum edge to edge hole spacing of 0.2 mm;

each hole being provided at the occlusal underside face of the ribbon with a respective funnel-like recess leading from the occlusal underside face to the remainder of the hole.

17. A traction ribbon spring as claimed in claim 16, wherein the hole at the distal end thereof is of larger diameter than the holes in the remainder of the spring operative portion to facilitate attachment of the distal end to an attachment point on one of the orthodontic devices.

18. A traction ribbon spring as claimed in claim 17, wherein a part of the operative portion immediately adjacent the larger diameter hole at the distal end is unperforated.

19. A traction ribbon spring as claimed in claim 16, wherein the diameter of the funnel recess mouth at the occlusal underside face is from 1.5 to 3 times the diameter of the hole.

20. A traction ribbon spring as claimed in claim 16, wherein the holes are of diameter 0.2 mm.

21. A traction ribbon spring as claimed in claim 16, wherein the holes are spaced longitudinally centre to centre from 0.5 mm to 1.0 mm.

22. A traction ribbon spring as claimed in claim 16, wherein the hole at the distal end thereof is of larger diameter than the holes in the remainder of he spring operative portion to facilitate attachment of the distal end to an attachment point on one of the orthodontic devices.

23. A traction ribbon spring as claimed in claim 16, and comprising at the mesial end of the operative portion an unperforated gripping portion to facilitate handling of the spring.

24. A traction ribbon spring as claimed in claim 16, wherein the mesial end of the spring is provided with a hole that is larger in diameter than the holes of the spring operative portion for attachment of a tension meter thereto.

25. A traction ribbon spring as claimed in claim 16, in combination with an orthodontic device having as attachment means for the spring a post protruding from a surface thereof with an enlarged head of greater diameter than the post, over which enlarged head the spring is forced against its resilience until it embraces the smallest diameter post and is retained by the head against removal from the post.

26. A method of making an elastomeric traction ribbon spring comprising a continuous ribbon of elastomeric material of substantially continuous width and thickness along its spring operative length, the ribbon having along its spring operative length a single row of longitudinally spaced holes, the holes each having at its occlusal underside face a respective funnel-like recess leading from the underside face to the remainder of the hole, the method including the steps of;

disposing the ribbon on an apertured die member having therein a sharp-edged aperture;

forcing into the ribbon and into the aperture concentrically therewith a conically tipped pointed punch of triangular transverse cross-section to force the resilient material of the ribbon into the aperture and thereafter to sever a piece of the ribbon thus forced into the aperature by engagement between the punch conical tip and the edge of the aperture to form such a hole with a funnel-like recess at the ribbon underside face.

* * * * *